United States Patent

Skakoon

[11] Patent Number: 5,308,333
[45] Date of Patent: May 3, 1994

[54] AIR ELIMINATING INTRAVENOUS INFUSION PUMP SET

[75] Inventor: James G. Skakoon, Melrose, Mass.

[73] Assignee: Baxter International Inc., Deerfield, Ill.

[21] Appl. No.: 66,916

[22] Filed: May 24, 1993

Related U.S. Application Data

[63] Continuation of Ser. No. 804,823, Dec. 6, 1991, abandoned.

[51] Int. Cl.⁵ .......................... A61M 1/00; A61M 5/00
[52] U.S. Cl. ........................................ 604/126; 604/247
[58] Field of Search ............... 604/122, 123, 126, 251, 604/247, 252, 256, 81, 82; 128/DIG. 12

[56] References Cited

U.S. PATENT DOCUMENTS

| | | | |
|---|---|---|---|
| 3,021,841 | 2/1962 | Burke | 604/252 X |
| 3,650,093 | 3/1972 | Rosenberg | 55/159 |
| 4,447,230 | 5/1984 | Gula et al. | 604/122 |
| 4,540,027 | 9/1985 | Forberg | 137/848 |
| 4,573,974 | 3/1986 | Ruschke | 604/81 |
| 4,642,098 | 2/1987 | Lundquist | 604/123 |
| 4,838,875 | 6/1989 | Somor | 604/262 |
| 4,941,875 | 7/1990 | Brennan | 604/81 |
| 4,950,254 | 8/1990 | Andersen et al. | 604/247 |
| 5,226,886 | 7/1993 | Skakoon et al. | 604/153 |

FOREIGN PATENT DOCUMENTS 2000685 1/1979 United Kingdom ............... 604/252

Primary Examiner—John D. Yasko
Assistant Examiner—Adam J. Cermak
Attorney, Agent, or Firm—Kane, Dalsimer, Sullivan, Kurucz, Levy, Eisele & Richard

[57] ABSTRACT

An intravenous set includes a spike or luer connector for receiving pharmaceutical product solution, a pumping section, an air eliminating filter, an anti-siphon valve and a connector for an IV access device. The air eliminating filter includes an in-line hydrophilic membrane and a hydrophobic membrane upstream thereof to vent trapped gases to the atmosphere. The anti-siphon valve has a positive crack pressure and is located downstream of the air eliminating filter.

11 Claims, 3 Drawing Sheets

AIR ELIMINATING INTRAVENOUS INFUSION PUMP SET

This is a continuation of copending application Ser. No. 07/804,823 filed on Dec. 6, 1991, now abandoned.

BACKGROUND OF THE INVENTION

2. Field of the Invention

This invention relates to an intravenous infusion pump set including an air eliminating filter with an in-line hydrophilic membrane to trap air in a medical infusion device line and a hydrophobic membrane to vent the trapped air. An anti-siphon valve with a positive crack pressure is situated in the line between the air eliminating filter and the infusion site.

2. Description of the Prior Art

The use of air eliminating filters in intravenous infusion pump sets is often required with the use of large volume pharmaceutical product bags due to the difficulty of purging all the air from the system. Furthermore, high infusion rate systems have an increased severity upon air embolism and therefore particularly require effective air elimination.

Air eliminating filters come in two different designs. The first design uses a standard hydrophilic membrane to prevent the passage of air bubbles and other gases through the apparatus. The pore size of a hydrophilic membrane is typically 0.2 micrometers. Hydrophilic membranes, when wetted, prevent the passage of air and gases therethrough up to the bubble point pressure but allow the passage of liquids therethrough. An intravenous set with an in-line hydrophilic membrane therefore allows a user to purge air from the intravenous set until liquid wets the filter and then no air will pass. The filter then collects air or gases on the upstream side of the membrane. Therefore, air accumulates during operation of the first design of filter thereby restricting flow of the liquid as air accumulates. The restriction increases until the flow stops when the membrane is covered by air thereby causing a complete occlusion.

The second design of filter used for air elimination includes an in-line hydrophilic membrane similar to the first design and additionally includes a vent covered with a hydrophobic membrane on the upstream side of the hydrophilic membrane housing thereby allowing the escape of the trapped gases. The hydrophobic membrane will allow only air (or gases) to pass therethrough thereby removing the trapped air from the filter. Therefore, this second design of filter will continue to pass the liquid from a liquid/air bubble mixture whereas the first design allows the bubbles to accumulate and eventually occlude the passage of liquid.

The use of this second design of filter which includes an in-line hydrophilic membrane and a hydrophobic membrane placed upstream of the hydrophilic membrane is well-known in the prior art. An example of such a filter is disclosed in U.S. Pat. No. 3,650,093 to Rosenberg.

However, as such prior art apparatus heretofore uses no anti-siphon or positive crack pressure valve means downstream of the filter, two problems will occur. Firstly, under certain common combinations of flow rate and resistance, lowering the infusion site relative to the filter will produce a negative pressure in the set resulting in air being admitted through the hydrophobic membrane. While this air can never pass through the hydrophilic membrane, its entry results in a bolus of pharmaceutical product to the patient. Secondly, if air exists in the filter either by incomplete purging, by entry from the pharmaceutical product container, or by prior admission through the hydrophobic membrane, elevation of the infusion site (such as may occur during ambulatory circumstances) will expel this air through the hydrophobic membrane. Retrograde blood flow from the patient will occur equal to the volume of air expelled.

An intravenous set which includes an air eliminating filter placed between the pharmaceutical product bag and the pump is similarly deficient. This location works well if the filter is always below the fluid level in the reservoir, as is common practice. However, if the pharmaceutical product bag of such a set is inadvertently or otherwise placed below the pump, then the air eliminating filter may draw air into itself and result in an error in flow rate or total occlusion. The air will not pass the hydrophilic membrane, but can cause air locking of the filter thereby preventing liquid from being drawn from the pharmaceutical product reservoir.

An intravenous set which includes an air eliminating filter between the pump and the patient is also deficient. If the patient is placed below the filter of such a set, the filter may draw in air from the atmosphere, particularly with low flow rates, thereby causing an additional error in flow rate. Further, if the patient is then moved from below the filter to above the filter, backflow of fluid from the patient to the filter will occur causing the intravenous set to fill with blood from the patient. Moreover, if the patient is below the pharmaceutical product bag and the set is not properly in the pump and therefore not occluded, a free flow, or siphoning, of solution into the patient will occur.

OBJECTS AND SUMMARY OF THE INVENTION

It is therefore an object of this invention to provide an intravenous set which prevents retrograde blood flow, unintended boluses of pharmaceutical product to the patient and air locking of the set, particularly due to negative system pressures.

It is therefore a further object of this invention to provide an intravenous set which includes an air eliminating filter and which prevents the occurrence of negative system pressures, particularly across the air eliminating filter.

It is therefore a still further object of this invention to provide an intravenous set which prevents negative system pressures under various combinations of flow rate, flow resistance and position of the intravenous set with respect to the infusion site.

It is therefore a still further object of this invention to provide an intravenous set which prevents free flow, or siphoning, of pharmaceutical product into the patient.

This invention is an intravenous set with a means for receiving pharmaceutical product, a pumping means, an air eliminating filter, an anti-siphon valve with positive crack pressure and a connector to attach to an intravenous access device. The air eliminating filter includes an in-line hydrophilic membrane to prevent the passage of air and gases therethrough and a hydrophobic membrane to vent the trapped air to the atmosphere. The anti-siphon valve with positive crack pressure is downstream of the air eliminating filter. The anti-siphon valve allows no forward flow until the crack pressure is exceeded. In other words, the valve prevents either forward flow when the pressure differential falls below the crack pressure or reverse flow. The use of the anti-siphon valve prevents negative system pressures within the intravenous set and any retrograde blood flow or unintended boluses associated therewith.

BRIEF DESCRIPTION OF THE DRAWINGS

Further objects and advantages of the invention will become apparent from the following description and claims, and from the accompanying drawings, wherein:

DETAILED DESCRIPTION OF THE PREFERRED EMBODIMENT

Figure 1:
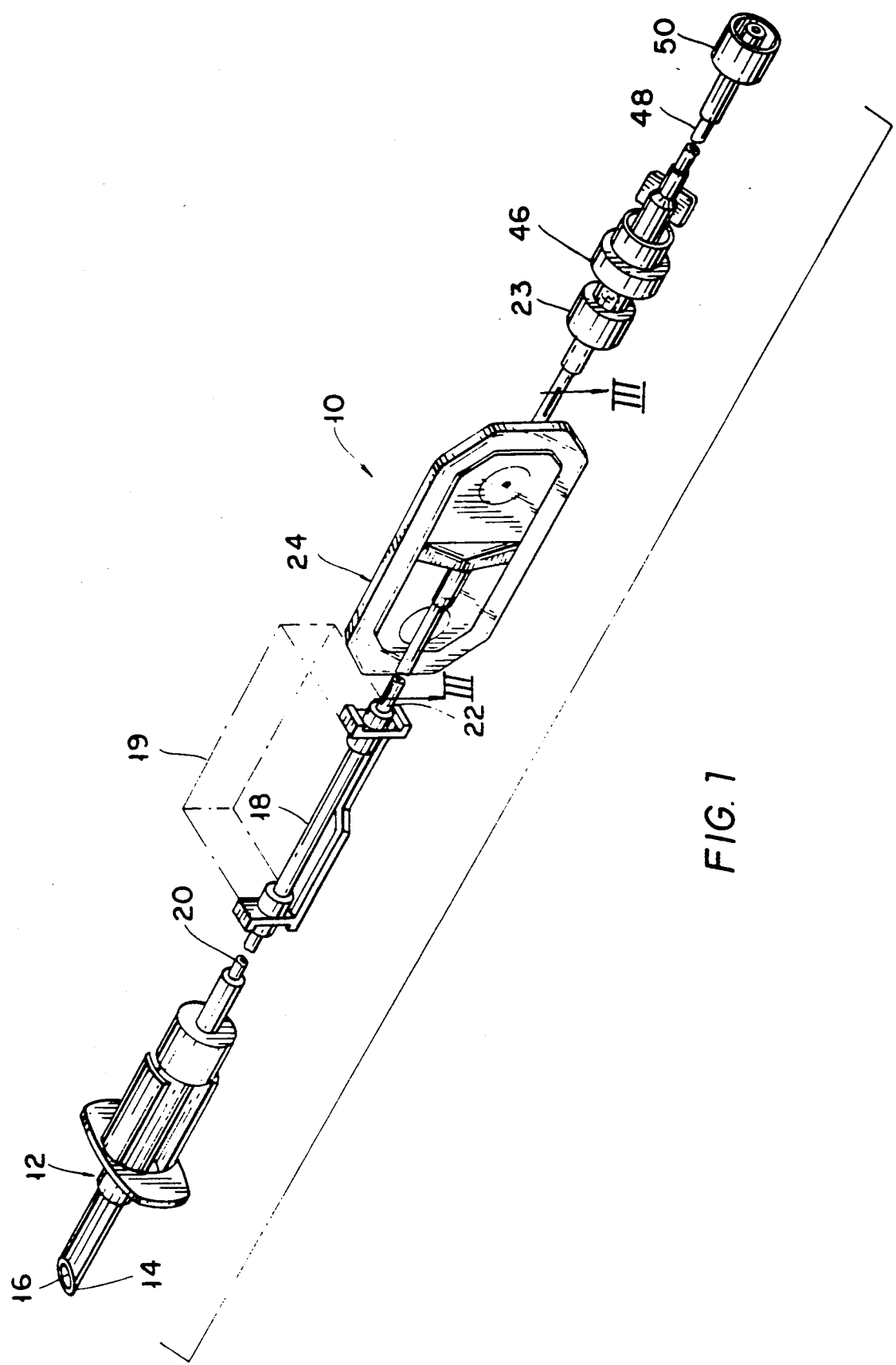
FIG. 1 discloses a perspective view of the air eliminating infusion pump set of the invention associated with an infusion pump shown in phantom.

Referring now to the drawings in detail wherein like numerals indicate like elements throughout the several views, intravenous set 10 includes spike 12 for engaging a pharmaceutical product bag (not shown). Spike 12 includes a pointed end 14 to enter the puncture port (not shown) of the pharmaceutical product bag. Spike 12 further includes lumen 16 for communicating pharmaceutical product therethrough to the pumping section 18 via tubing 20.

Figure 4:
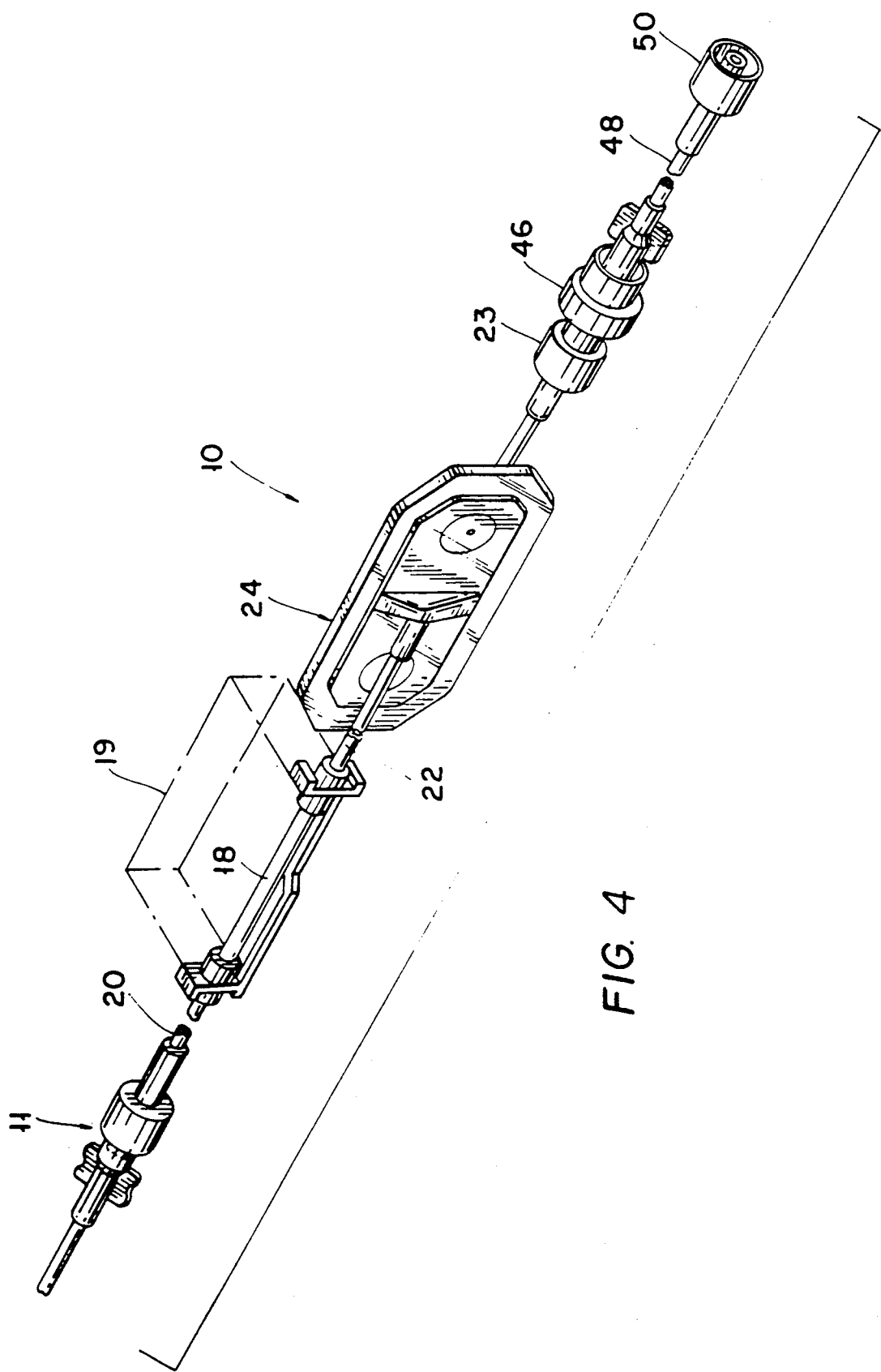
FIG. 4 is a view similar to FIG. 1 disclosing an alternate embodiment of air eliminating infusion pump set with a Luer connector substituted for the spike.

Spike 12 may be replaced with any means for engaging a source of pharmaceutical product. A Luer connector 11 (see FIG. 4) is a particularly frequent substitution for spike 12.

Pumping section 18, in conjunction with an infusion pump 19, shown in phantom, propels the pharmaceutical product from spike 12 downstream to air eliminating filter 24 through tubing 22. Tubing 22 may include a luer connector set 23 to allow the interchangeable engagement of various components of intravenous set 10. A typical infusion pump 19 usable with the invention may include a linear peristaltic mechanism.

Figure 2:
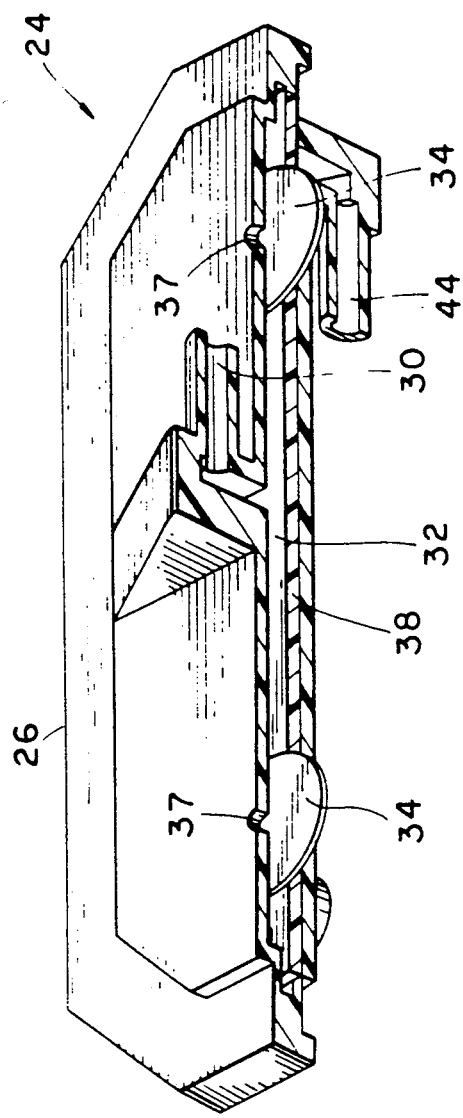
FIG. 2 is an enlarged fragmentary perspective view, partly in section, of the air eliminating filter.
Figure 3:
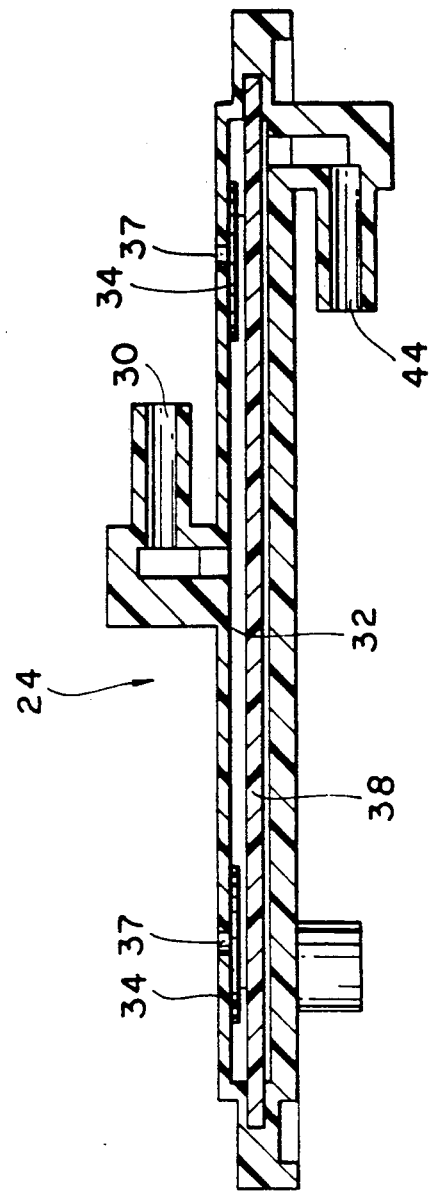
FIG. 3 is a cross sectional view of the filter along plane 2—2 of FIG. 1.

As shown in FIGS. 2 and 3, air eliminating filter 24 includes a body 26 having fluid input port 30 adapted to be coupled with tubing 22. Input port 30 leads to internal chamber 32 which includes hydrophobic membranes 34. Air and other gases trapped in chamber 32 can pass through hydrophobic membranes 34 and passageway 37 to the atmosphere. Internal chamber 32 further includes hydrophilic membrane 38 spaced parallel to hydrophobic membranes 34. Liquids pass through hydrophilic membrane 38 to exit port 44. Exit port 44 is in fluid communication with anti-siphon valve 46 (see FIG. 1) which in turn is coupled with and in fluid communication with tubing 48.

Anti-siphon valve 46 is a check valve with a positive crack pressure. Valve 46 prevents reverse flow through tube set 10 (i.e. from valve 46 to filter 24) and allows forward flow (i.e. from filter 24 to valve 46) only when the pressure differential across valve 46 is greater than the crack pressure of said valve 46. Further, valve 46 reseals to prevent further forward flow whenever the pressure across valve 46 falls below said positive crack pressure. This arrangement precludes any retrograde fluid flow (e.g. blood) from occurring. Also, importantly, this arrangement guarantees that the pressure within tube set 10 between pumping section 18 and valve 46, and particularly within filter 24 is always above atmospheric pressure by at least the crack pressure of valve 46 thereby precluding admission of atmospheric air into filter 24 through hydrophobic membrane 34.

The present invention contemplates a valve 46 with a crack pressure of 1.5 to 3.5 psi. This is above the range of commonly encountered head pressures and is thereby effective in preventing both uncontrolled free flow, or siphoning, and admission of air into the filter. A valve of this type is disclosed in U.S. Pat. No. 4,535,820.

Tubing 48 engages luer connector 50. Luer connector 50 is used to adapt to an IV access device which engages the patient.

To use this intravenous set 10, the user employs commonly accepted IV techniques.

Thus, the several aforementioned objects and advantages are most effectively attained. Although a single preferred embodiment of the invention has been disclosed and described in detail herein, it should be understood that this invention is in no sense limited thereby and its scope is to be determined by that of the appended claims.

What is claimed is:

1. An intravenous set having an upstream end and a downstream end and comprising:
   receiving means for receiving a supply of pharmaceutical product solution at the upstream end;
   peristaltic pumping section means in fluid communication with said receiving means, said peristaltic pumping section means being arranged and constructed to interface with a peristaltic pump;
   an air eliminating filter in fluid communication with said pumping section means for receiving said solution propelled by said peristaltic pump form said receiving means;
   a positive crack pressure anti-siphon valve downstream from said air eliminating filter, wherein said valve is arranged to maintain said solution within said eliminating filter at a preselected threshold level above atmospheric pressure, wherein said valve precludes flow of solution through sad valve in the direction of said means for receiving a supply of pharmaceutical product solution and wherein said valve seals to prevent flow of solution through said valve away from said means for receiving a supply of pharmaceutical product solution when pressure across said valve as measured from said air eliminating filter to atmosphere falls below a predetermined positive threshold; and
   means for engaging an IV access device downstream from said valve at the downstream end.

2. The intravenous set of claim 1 wherein said means for receiving pharmaceutical product solution includes a spike with a lumen therethrough.

3. The intravenous set of claim 1 wherein the means for receiving pharmaceutical product solution includes a first LUER connector means.

4. The intravenous set of any of claims 1, 2 or 3 wherein said air eliminating filter includes a first membrane which allows the passage of liquid therethrough but which precludes the passage of gas therethrough and a second membrane which allows the passage of gas to vent to the atmosphere but which precludes the passage of liquids therethrough.

5. The intravenous set of claim 4 wherein said first membrane is a hydrophilic membrane and wherein said second membrane is a hydrophobic membrane.

6. The intravenous set of claim 4 wherein said pumping section means and said air eliminating filter are in fluid communication via a second Luer connector.

7. The intravenous set of claim 4 wherein said means for engaging an IV access device includes a further Luer connector.

8. An intravenous set having an upstream end and a downstream end and including:

receiving means for receiving a supply of pharmaceutical product solution at the upstream end;

peristaltic pumping section means in fluid communication with said receiving means for receiving a supply of pharmaceutical product solution;

an air elimination filter in fluid communication with said pumping section means for receiving said solution propelled by said peristaltic pump from said receiving means;

a positive crack pressure anti-siphon valve downstream from said air eliminating filter wherein said valve is arranged to maintain said solution in said air elimination filter at a preselected threshold level above atmospheric pressure;

wherein said valve seals to prevent flow of solution through said valve when pressure across said valve as measured from said air eliminating filter to atmosphere falls below a predetermined positive threshold; and means for engaging an IV access device downstream from said valve at the downstream end.

9. The intravenous set of claim 8 wherein said positive crack pressure valve includes means that prevent free flow of solution into a patient.

10. The intravenous set of claim wherein said valve precludes flow of solution through said valve in the direction of said means for receiving a supply of pharmaceutical product solution.

11. The intravenous set of claim 8 wherein said valve has a crack pressure of between 1.5 and 3.5 psi.

* * * * *

UNITED STATES PATENT AND TRADEMARK OFFICE
CERTIFICATE OF CORRECTION

PATENT NO. : 5,308,333
DATED : May 3, 1994
INVENTOR(S) : James G. Skakoon

It is certified that error appears in the above-indentified patent and that said Letters Patent is hereby corrected as shown below:

```
Column 3, line 40, change "luer" to --Luer--
Column 4, line 12, change "luer" to --Luer--
Column 4, line 35, change "form" to --from--
Column 4, line 42, change "sad" to --said--
Claim 10, line 1, after "claim" insert --8--.
```

Signed and Sealed this

Sixth Day of June, 1995

Attest:

Attesting Officer

BRUCE LEHMAN

Commissioner of Patents and Trademarks